United States Patent [19]

Zimmon

[11] Patent Number: 5,653,240
[45] Date of Patent: Aug. 5, 1997

[54] METHOD AND DEVICE FOR MEASURING PORTAL BLOOD PRESSURE

[76] Inventor: David S. Zimmon, 7 Farm View Rd., Port Washington, N.Y. 11050

[21] Appl. No.: 227,064

[22] Filed: Apr. 13, 1994

Related U.S. Application Data

[60] Continuation-in-part of Ser. No. 101,910, Aug. 4, 1993, which is a division of Ser. No. 781,224, Dec. 30, 1991, Pat. No. 5,308,326, which is a continuation of Ser. No. 372,875, Jun. 28, 1989, abandoned.

[51] Int. Cl.⁶ ............................................. A61B 5/0215
[52] U.S. Cl. ........................................... 128/673; 128/748
[58] Field of Search ................................. 128/673, 675, 128/748; 604/96–104; 606/192

[56] References Cited

U.S. PATENT DOCUMENTS

| | | |
|---|---|---|
| 3,055,371 | 9/1962 | Kulick . |
| 4,204,525 | 5/1980 | Olson . |
| 4,214,593 | 7/1980 | Imbruce et al. . |
| 4,367,747 | 1/1983 | Witzel . |
| 4,735,194 | 4/1988 | Stiegmann . |
| 4,832,691 | 5/1989 | Witzel ................................... 606/192 |
| 4,981,470 | 1/1991 | Bombeck, IV . |
| 5,181,517 | 1/1993 | Hickey . |
| 5,247,938 | 9/1993 | Silverstein et al. ................ 128/662.03 |

*Primary Examiner*—Angela D. Sykes
*Attorney, Agent, or Firm*—Woodard, Emhardt, Naughton Moriarity & McNett

[57] ABSTRACT

A method and a device to measure portal blood pressure with an endoscope and an inflatable balloon inserted into the esophagus and positioned at the diaphragmatic hiatus. A balloon mounted over a tube is placed within the diaphragmatic hiatus and gradually inflated through a lumen that runs from the balloon to a position that is external from the patient. The pressure within the balloon is increased until the blood flow in the collateral portal hepatic veins that traverse the diaphragm at this location are occluded. The occlusion of the blood flow is signaled when esophageal varices visible above the balloon collapse. The internal balloon pressure required to occlude the blood flow in these collateral portal veins is approximately equivalent to the pressure in the main portal vein.

23 Claims, 10 Drawing Sheets

METHOD AND DEVICE FOR MEASURING PORTAL BLOOD PRESSURE

This is a continuation in part of prior application Ser. No. 08/101910, filed Aug. 4th, 1993; which is a divisional of prior application Ser. No. 07/781,224, filed Dec. 30th, 1991 now U.S. Pat. No. 5,308,326; which is a continuation of prior application Ser. No. 07/372,875, filed Jun. 28, 1989, now abandoned; which are all incorporated into this specification by reference.

BACKGROUND OF THE INVENTION

This invention generally pertains to a method and a device for measuring portal blood pressure, and more particularly pertains to a method and a device that use an inflatable balloon inserted into the esophagus.

A high pressure gradient typically exists across a diseased or damaged liver, between the portal and hepatic veins. The development of this restriction through the liver causes blood to bypass the liver and forces blood into collateral blood vessels within and around the upper stomach and lower esophagus. As a result, esophageal and gastric veins bulge inside the gastrointestinal lumen and are visible as gastrointestinal varices under upper gastrointestinal endoscopy. If the portal blood pressure exceeds 21 mmHg, the varices often rupture and produce a life threatening hemorrhage. However, this often fatal and always serious bleeding can be prevented by prophylactic drug therapy.

Accordingly, patients with liver disease are placed under surveillance and watched for portal hypertension and risk of gastrointestinal bleeding. If their portal pressure is greater than 22 mmHg or their portal-hepatic pressure gradient is greater than 12 mmHg, the patients are treated with beta blockade. During this drug treatment, the portal blood pressure of a patient remains under watch. Further surveillance determines if they are properly responding to beta blockade, determines if there is a need for other drugs to reduce portal blood pressure, and generally monitors the effect of therapy on the patient. The more acute and severe the patient's liver disease, particularly if the patient is suffering from upper gastrointestinal bleeding, the more important is the measurement of portal pressure and the patient's response to therapy.

The traditional methods of measuring portal pressure require entry into an hepatic or portal vein. The percutaneous method can be applied on ambulatory or hospitalized patients who do not have a bleeding diathesis or advanced cirrhosis with portal hypertension. In this technique, under local anesthesia, a fine gauge needle is inserted into the veins under fluoroscopic control. In a fashion similar to that for performing percutaneous cholangiography, the needle is manipulated into a portal vein and its position confirmed by injecting a small amount of contrast. The portal pressure is then measured. The needle is then manipulated into a hepatic vein, also confirmed by injection of a small amount of contrast, and the hepatic venous pressure is measured. The difference between the portal and hepatic pressure is calculated as the portal-hepatic pressure gradient. Gradients greater than 12 mmHg indicate a risk of variceal hemorrhage.

Measurement of portal pressure by transvenous catheterization is done in a similar fashion. The hepatic vein is entered with a standard cardiovascular catheter through either a femoral, internal jugular, or medial antecubital approach under local anesthesia. The catheter is advanced under fluoroscopy into a hepatic vein and wedged closed, typically with a balloon catheter. With the vein blocked, there is a stasis column of blood extending from the hepatic vein to the portal vein in patients with cirrhosis, and portal pressure is similar or identical to the occluded or wedged hepatic venous pressure. The non-wedged hepatic venous pressure or inferior vena caval pressure is then measured and the difference is calculated as the portal-hepatic pressure gradient.

Both of these preceding methods are expensive procedures using complex methods and specialized techniques. They are rarely used by gastrointestinal endoscopists. It would be of great value if portal pressure could be more easily measured during gastrointestinal endoscopy, perhaps in a more simple and less obtrusive fashion.

Measurement of portal pressure should be differentiated from pressure within esophageal varices and the measurement thereof. Pressure in portal-systemic collateral vessels (esophagogastric varices) is related to but not identical to portal pressure because the collateral vessels are part of a resistance loop between pressure in the portal vein and the systemic exit point of the collateral vein. Furthermore in the clinical situation where physiologic variables (changes in blood volume) or drug therapy (beta blockade) directed at changing (reducing) portal pressure and splanchnic blood inflow are operating the relationship between portal pressure and variceal pressure would be variable. Consequently in any individual situation the relationship between variceal pressure and portal pressure cannot be known without a comparative measurement. Therefore direct measurement of portal pressure is essential.

SUMMARY OF THE INVENTION

The object of this invention is to provide a device and a technically simple method for measuring portal venous pressure in patients with esophageal varices during upper gastrointestinal endoscopy. An advantage of this invention is that it allows endoscopic surveillance of esophageal varices combined with measurement of portal venous pressure in a brief procedure without significantly increasing risk above that associated with upper gastrointestinal endoscopy, alone.

In general, this invention is a method and a device to measure the portal blood pressure in the venous circulation system and is typically performed or used during gastrointestinal endoscopy. Included in the method to practice this invention is the step of passing an esophageal inflatable balloon down the esophagus of a patient and positioning the esophageal inflatable balloon inside the esophagus at a position where the esophagus passes through the muscular diaphragm. This opening in the muscular diaphragm is known as the diaphragmatic hiatus. Accordingly, to practice this invention the esophageal inflatable balloon is placed within the esophagus, at a position within the diaphragmatic hiatus, which is in the spatial plane of the muscular diaphragm.

The device for measuring portal blood pressure comprises an elongate member, an esophageal inflatable balloon having low compliance over its working pressure range mounted over the elongate member, and an inflation lumen opening into the esophageal balloon. Furthermore, during use, the device is typically connected to a means for measuring the pressure inside the esophageal inflatable balloon. The elongate member is useful to guide the esophageal inflatable balloon into the diaphragmatic hiatus. The elongate member may, itself, be of a length to place the esophageal inflatable balloon in position; however, the use of other members to place the elongate member and esophageal inflatable balloon into the diaphragmatic hiatus is also contemplated by the method aspect of this invention. An example of another member includes a separate member of a length sufficient to push the elongate member and esophageal inflatable balloon into the diaphragmatic hiatus. A further example of other members include an endoscope or guidewire, over which the elongate member may slide, and a split overtube to push the elongate member and the esophageal inflatable balloon over the endoscope or guidewire and into the diaphragmatic hiatus.

Once the esophageal balloon is placed within the diaphragmatic hiatus, the portal blood pressure is measured. An endoscope is positioned above the esophageal inflatable balloon to observe varicose veins in the walls of the esophagus, known as esophageal varices. The esophageal inflatable balloon is then gradually inflated until the esophageal varices collapse. Collapse of these endoscopically visible esophageal varices signals that portal blood flow to the varices has ceased and that the collateral portal veins traversing the diaphragmatic hiatus are occluded. The balloon pressure required to occlude these portal collateral veins is about identical to the pressure in the main portal vein.

A preferred device used to measure portal blood pressure includes an elongate member preferably adapted to allow the equalization of pressure between the stomach and the esophagus during the inflation of the esophageal balloon. The elongate member has proximal and distal ends. The esophageal inflatable balloon is mounted near the distal end and over the exterior of the elongate member. The pressure equalization is attained by an open channel that runs from an opening above the esophageal balloon, through the elongate member, and to an opening below the esophageal balloon leading to the stomach. To date, a preferable embodiment is an elongate member comprising a tube with open proximal and distal ends.

The elongate member is also preferably adapted to extend up the esophagus to a position external of the patient. This configuration allows the device to be pulled and placed in traction by maintaining tension upon the inflated device, or also allows the deflated device to be grasped and completely removed. A preferred embodiment of this aspect of the invention is a bridle. The bridle is configured to extend up the esophagus to allow the device to be secured in place with the proximal end of the elongate member positioned within the digestive tract. In another preferred embodiment of this aspect, the proximal end of the elongate member itself extends externally of the patient, upon which traction may be applied or the device grasped for removal.

BRIEF DESCRIPTION OF THE DRAWINGS

In the accompanying drawings, forming a part of this specification, and in which like numerals are employed to designate like parts throughout the drawings.

DESCRIPTION OF THE PREFERRED EMBODIMENTS

Specific language is used to describe several embodiments of this invention for the purpose of promoting an understanding of the principles of this invention. However, it must be understood that the extent of this invention is not limited by using this specific language. Any alteration and further modification of the described method and any application of the principles of this invention are also intended that normally would occur to one skilled in the art to which this invention pertains.

Figure 1:
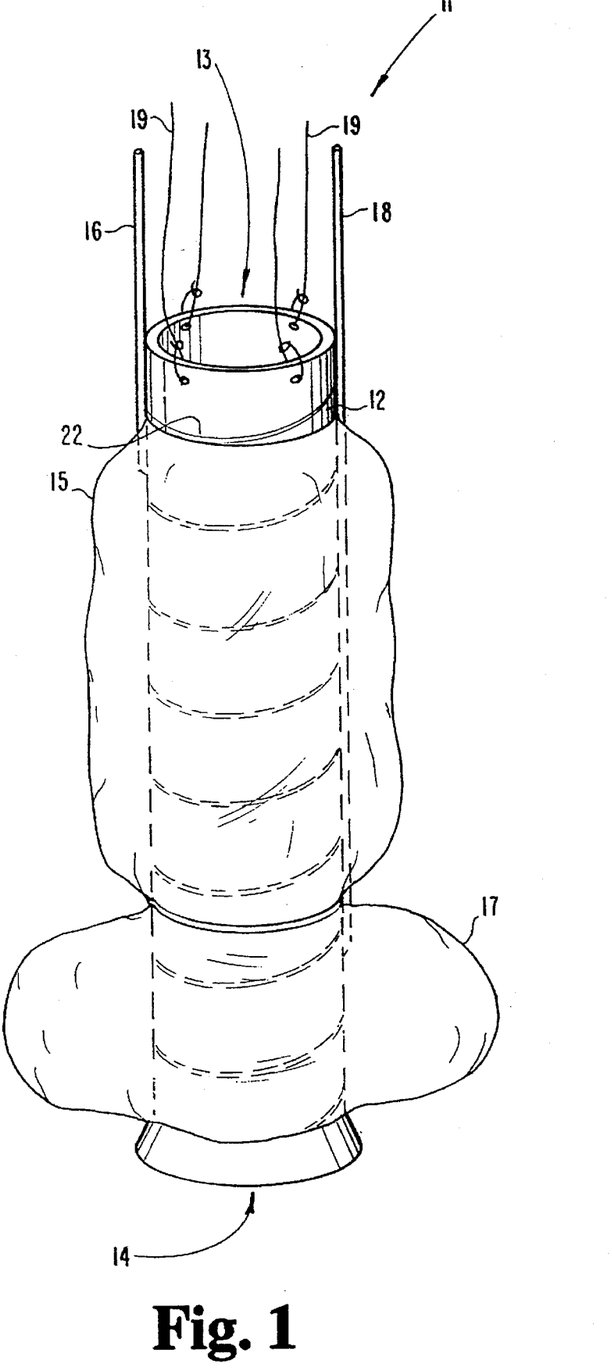
FIG. 1 is a perspective view of one embodiment of a device used to practice this invention, for illustrative purposes, the full lengths of the wires 19 and of the lumens 16 and 18 are not shown.

Referring to FIG. 1, a preferred esophago-gastric balloon device 11 is shown. The device 11 includes an elongate member 12, preferably a tube, having a proximal end 13 and a distal end 14, where both ends are preferably open. An esophageal inflatable balloon 15 is mounted over the elongate member 12, and an inflation lumen 16 is provided for directing pressurized fluid in and out the esophageal inflatable balloon 15. Optionally, a gastric inflatable balloon 17 is mounted over the elongate member 12 and is adapted to seat against the gastric cardia when inflated in the stomach, and when the device 11 is pulled by the wires 19 in a direction up the esophagus. A separate inflation lumen 18 is provided to inflate and deflate the gastric inflatable balloon 17.

The elongate member 12 of a preferred device 11 may be made of plastic or other suitable material. The elongate member 12 can be of any length. If may be of a length to place the esophageal inflatable balloon 15 directly into position and simultaneously externally extend from the patient or it may be of a length such that, when the device 11 is in place, the elongate member 12 does not externally extend from the patient. The elongate member 12 may be of any cross-sectional configuration such as round, polygonal, or irregular, but is preferably round. The elongate member 12 may be solid or hollow, but is preferably hollow with open proximal and distal ends to provide an inner lumen. The inner lumen allows for the equalization of pressure between the stomach and the esophagus during a portal blood pressure measurement. The elongate member 12 is also sufficiently rigid such that, when the esophageal inflatable balloon 15 and optionally the gastric inflatable balloon 17 are inflated, the elongate member 12 does not collapse, but rather continues to provide a passage through the inner lumen. In a preferred embodiment, the elongate member 12 is a tube of approximately 8 centimeters in length and is translucent or substantially transparent. Additionally, in a preferred embodiment, the elongate member 12 contains an imbedded wire coil 22 to render the device visible under roentgenographic examination to monitor its position in the patient. The coil 22 may also serve to help prevent the collapse of the elongate member 12.

It is also preferred that the elongate member 12 have an inner diameter of about 1.3 cm and an outer diameter of about 1.5 cm. The 1.2 cm inner diameter is preferred so that even the largest operating upper gastrointestinal endoscopes can be effectively used in connection with the device 11. It is understood, however, that elongate members having other dimensions could be used in this invention.

The esophageal inflatable balloon 15 is mounted over the elongate member 12. In a preferred device, the esophageal inflatable balloon 15 has a length of about 4 centimeters, but may be of any length necessary to lie across the patients diaphragmatic hiatus. Also, in a preferred device, the esophageal inflatable balloon 15 is of a size such that, when inflated, the greatest outer diameter of the device 11 across the inflated esophageal inflatable balloon 15 is about 3.0 cm. It is understood, however, that the size of the esophageal inflatable balloon 15 can be any size sufficient to fill a particular patient's diaphragmatic hiatus. As to the method of mounting the esophageal inflatable balloon over the tube, it may be mounted by silk ties, bonding or vulcanizing, or any other suitable airtight manner known in the art.

An inflation lumen 16 for directing pressurized fluid to inflate the esophageal inflatable balloon 15 is also provided and preferably is bonded to the side of the elongate member 12. This lumen 16 may be any suitable lumen known in the art for this purpose, and has at least one opening into the esophageal inflatable balloon 15, and is of sufficient length to extend up the esophagus and externally extend from the patient when the device 11 is in place.

In a preferred or optional embodiment of the device 11, a gastric inflatable balloon 17 is mounted over the elongate member 12 near its distal end 14 to provide a seating surface within the stomach. The gastric inflatable balloon 17 has an inflated diameter which is sufficiently large, so that when positioned in the stomach and inflated, the gastric inflatable balloon 17 seats against and compresses the gastric cardia when the device 11 is pulled by the wires 19, or pulled by the proximal end of the elongate member 12 in a direction up the esophagus. In a preferred device, the gastric inflatable balloon 17 is of a size that when inflated, the greatest outer diameter of the device 11 across the gastric inflatable balloon 17 is about 6.0 cm. The gastric inflatable balloon 17 can be mounted using silk ties, bonding or vulcanizing, or any other suitable airtight method known in the art. An inflation lumen is also provided to direct pressurized fluid to inflate the gastric inflatable balloon 17. This lumen could be the same one which inflates the esophageal inflatable balloon 15, but in a preferred device, a second and separate inflation lumen 18 is provided for the gastric inflatable balloon 17, and is also bonded to the side of the elongate member 12. The inflation lumen 18 passes through the esophageal inflatable balloon 15 and into the gastric inflatable balloon 17, opening only into the latter. This enables the selective inflation of the esophageal inflatable balloon 15 and the gastric inflatable balloon 17.

Both the esophageal inflatable balloon and the gastric inflatable balloon are preferably fabricated to have low compliance, that is, less than about a 10% change in volume, over the working pressure range of about 20 mmHg to about 60 mmHg.

A preferred device 11 also includes a plurality of wires 19 which are attached to the elongate member 12 and generally form a bridle. In the preferred device 11, the wires 19 are of sufficient length that, when the device 11 is in place, the wires 19 extend up the esophagus and externally extend from the patient. Thus, the bridal is adapted and operable to allow the device 11 to be secured in place in the patient while having the proximal open end 13 of the elongate member 12 positioned within the esophagus. This provides a convenient passage through which materials may pass to the stomach and enables normal feeding and swallowing. The wires 19 are attached to the elongate member 12 by securing them through small apertures 20 provided near the proximal open end 13 of the elongate member 12. It is understood, however, that bonding or any other suitable means known in the art could be used to attach the wires 19 to the elongate member 12. In a preferred device 11, four wires 19 are attached to the elongate member 12, but it is understood that three or any other number sufficient to provide stabilization and securing of the device would be adequate. The wires 19 may be constructed of stainless steel or any other suitable material known in the art; however, it is preferred that they be made of or comprise a suitable radiopaque material, such as platinum, to aid in monitoring the placement of the device 11. Furthermore, it must be understood that although the bridle is shown, it is also contemplated that elongate member 12 could continue up the esophagus, externally extend from the patient, and that proximal end 13 could attach to a device to pull elongate member 12 and place the device 11 in traction.

Further details regarding the device can be found in Balloon Tamponade Devices and Methods for their Placement, U.S. application Ser. No. 07/781,224 filed Dec. 30, 1991, which is incorporated into this specification by reference.

As an initial step to practice this invention, the device is passed down the esophagus, to a location within the patient's diaphragmatic hiatus. Preferably, the device is placed into this position during upper gastrointestinal endoscopy. For example, prior to passing an endoscope down the esophagus, the device is backloaded on the endoscope by passing the endoscope through the open ends of the device. The endoscope is then passed through the patient's mouth, down the esophagus, and into the stomach, usually a distance of about 50 cm past the patient's incisors.

Figure 2:
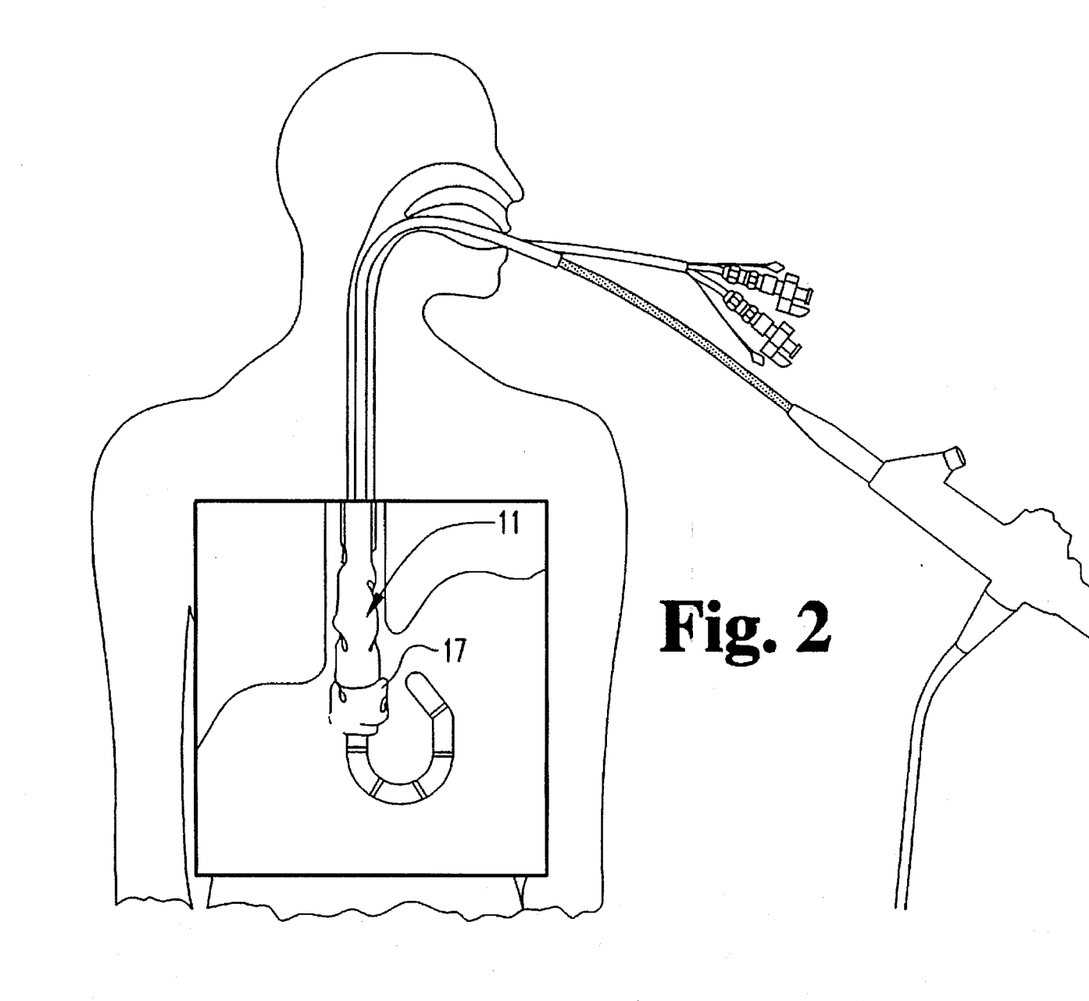
FIGS. 2 to 10 are step-by-step sectional views of the device illustrated in FIG. 1 being placed in a patient, according to one embodiment of this invention.

Next and referring to FIG. 2, the device 11 is advanced down over the endoscope using a split overtube until the gastric inflatable balloon 17 is positioned within the stomach while leaving at least a portion of the bridle or the elongate member external to the patient. In this fashion, the endoscope acts as an internal guide to properly place the device 11. In most normal adults, when the overtube has been advanced to a distance of 36 cm from the patient's incisors, the gastric inflatable balloon is properly positioned within the stomach.

Figure 3:
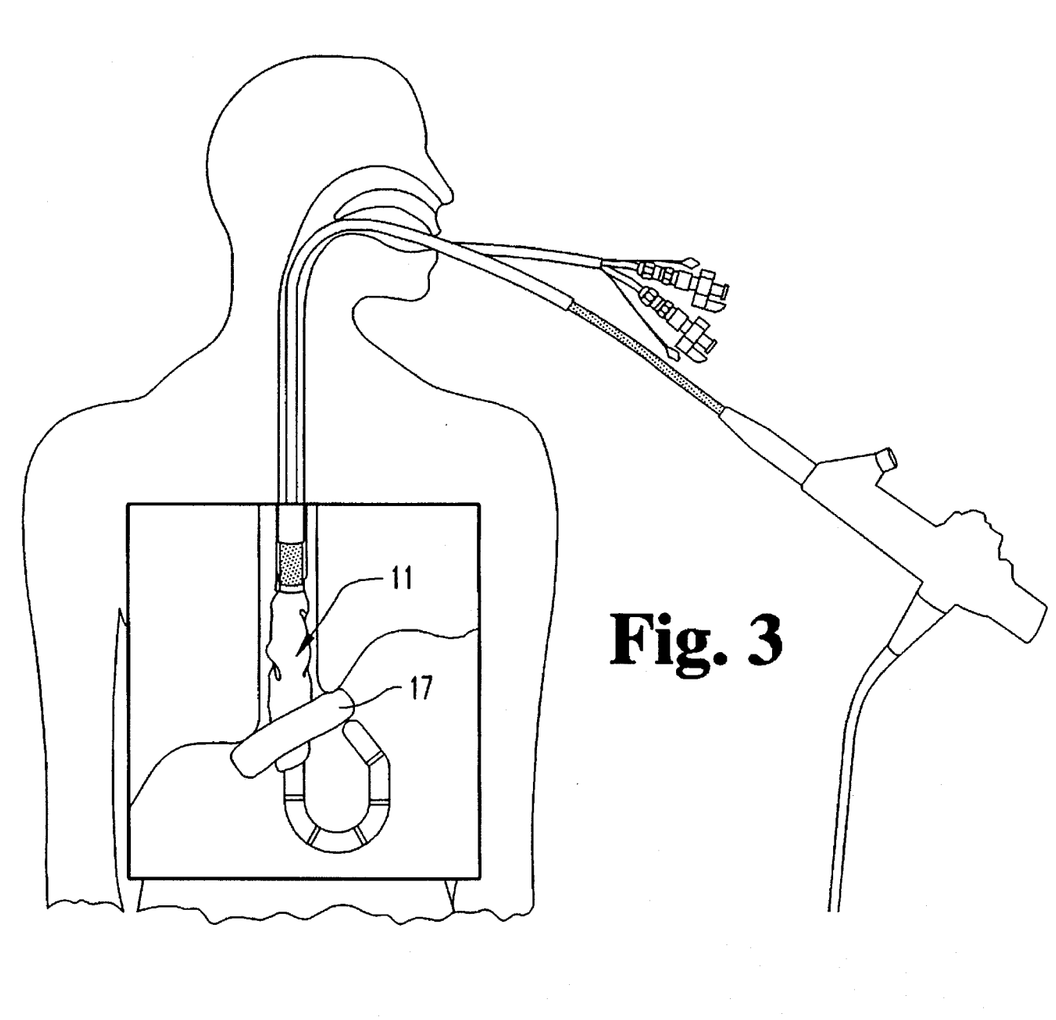

Referring to FIG. 3, the gastric inflatable balloon 17 is inflated and the elongate member or bridle wires are pulled until the gastric inflatable balloon is felt to seat against the gastric cardia. Once in position, the pressure within the gastric inflatable balloon is preferably adjusted to about 20 mmHg. A significant advantage of using an endoscope as a guide means is that the endoscope can be used to monitor the position of the device 11 both during and after the placement procedure. As shown, an endoscopic "U" turn is performed in the stomach to view the placement of the device from below, after the device 11 is in place. This procedure is particularly preferable when an esophageal inflatable balloon is utilized without a gastric inflatable balloon.

Figure 4:
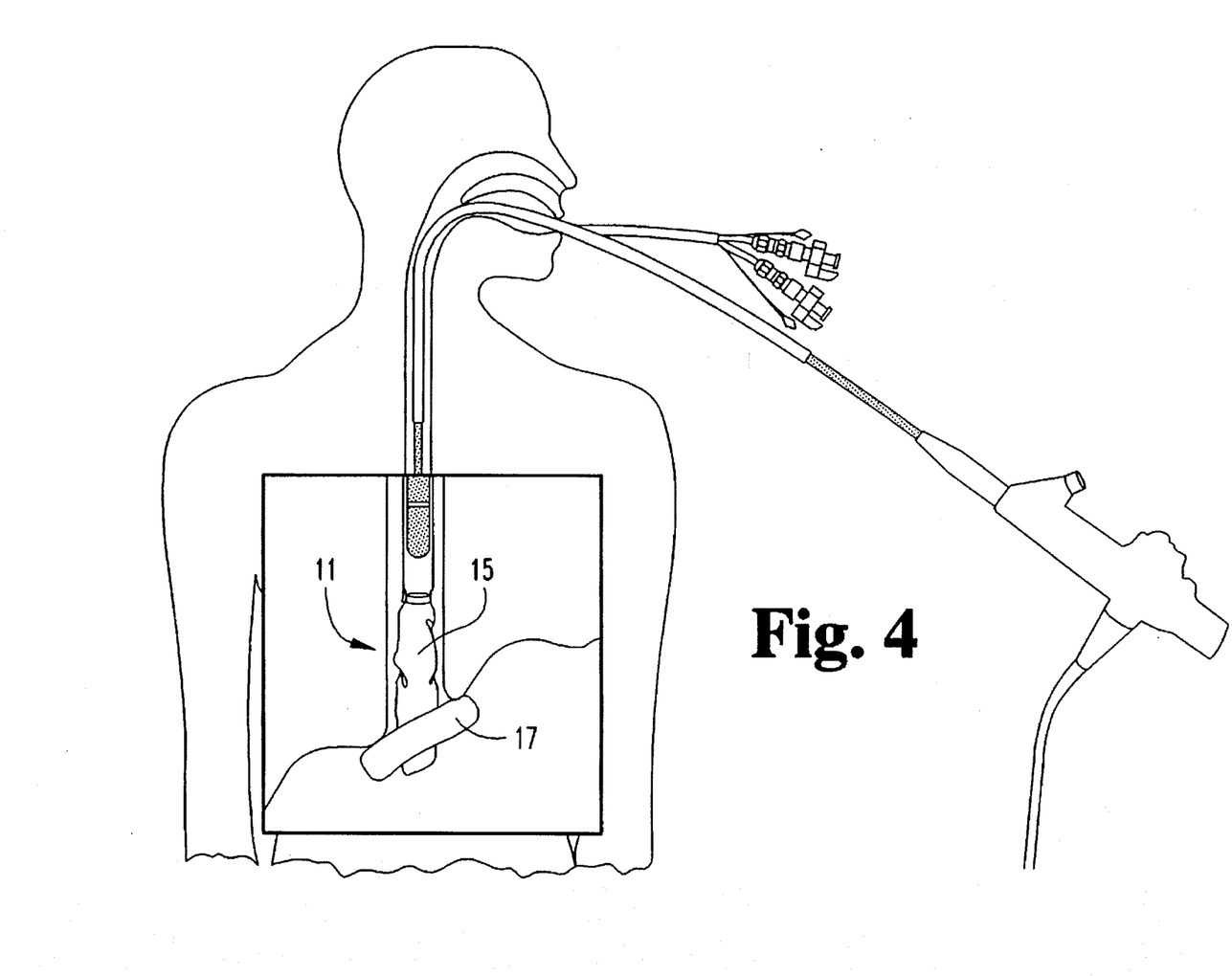

Referring to FIG. 4, after the inflation of the gastric inflatable balloon 17 and its placement against the gastric cardia, the endoscope is withdrawn from the stomach to a location above the device 11. At this location, esophageal varices above the esophageal inflatable balloon 15 are visible with the endoscope.

Figure 5:
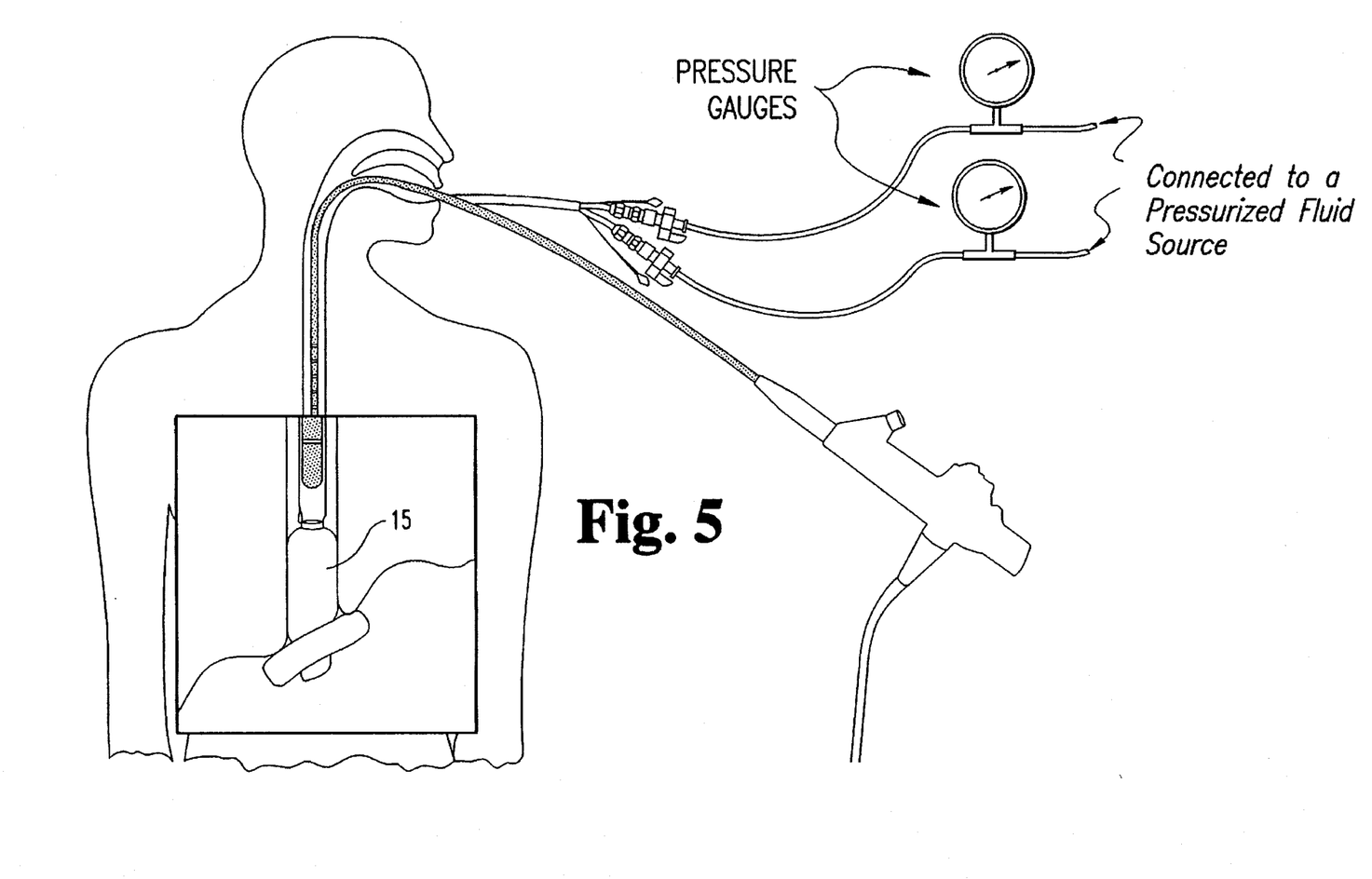

Referring to FIG. 5, the esophageal inflatable balloon 15 is then inflated to fix the device 11 into position by compressing the diaphragmatic hiatus and surrounding tissue. A preferable initial inflation pressure is about 20 mmHg. An aneroid or mercury manometer can be used to make these and other pressure measurements required in this invention. Once device 11 is fixed, the external pulling or traction to device 11 is then preferably released. The release of traction allows the patient's diaphragm to move in normal respiration which otherwise might prevent an accurate measure of the patient's portal blood pressure.

As an alternative method of placement, the device 11 may be placed using a balloon introducer such as model number WCPI-1 Prosthesis Introducer manufactured by Wilson-Cook Medical, Inc., of Winston-Salem, N.C., or, during a preceding endoscopy, a wire guide can be passed, and the device 11 can be introduced loaded on a dilator such as a Savory dilator such as model number SGD 14-100 also manufactured by Wilson-Cook Medical, Inc.

Or as another alternative, the elongated member may be sufficiently long and rigid to introduce and pass the esophageal inflatable balloon down the esophagus without the need of a guide. The esophageal inflatable balloon, mounted over the distal end of the elongate member, is directed into the diaphragamatic hiatus by pushing the elongate member down the patient's esophagus. Once in position, the esophageal inflatable balloon is inflated and fixed into position by compressing against the diaphragmatic hiatus and surrounding tissue. The esophageal inflatable balloon is then further inflated and deflated, as needed, to measure portal blood pressure. In this embodiment, it is preferable that the proximal end of the elongate member remain external of the patient where it may be grasped for removal or pulled to place the device in traction.

Figure 6:
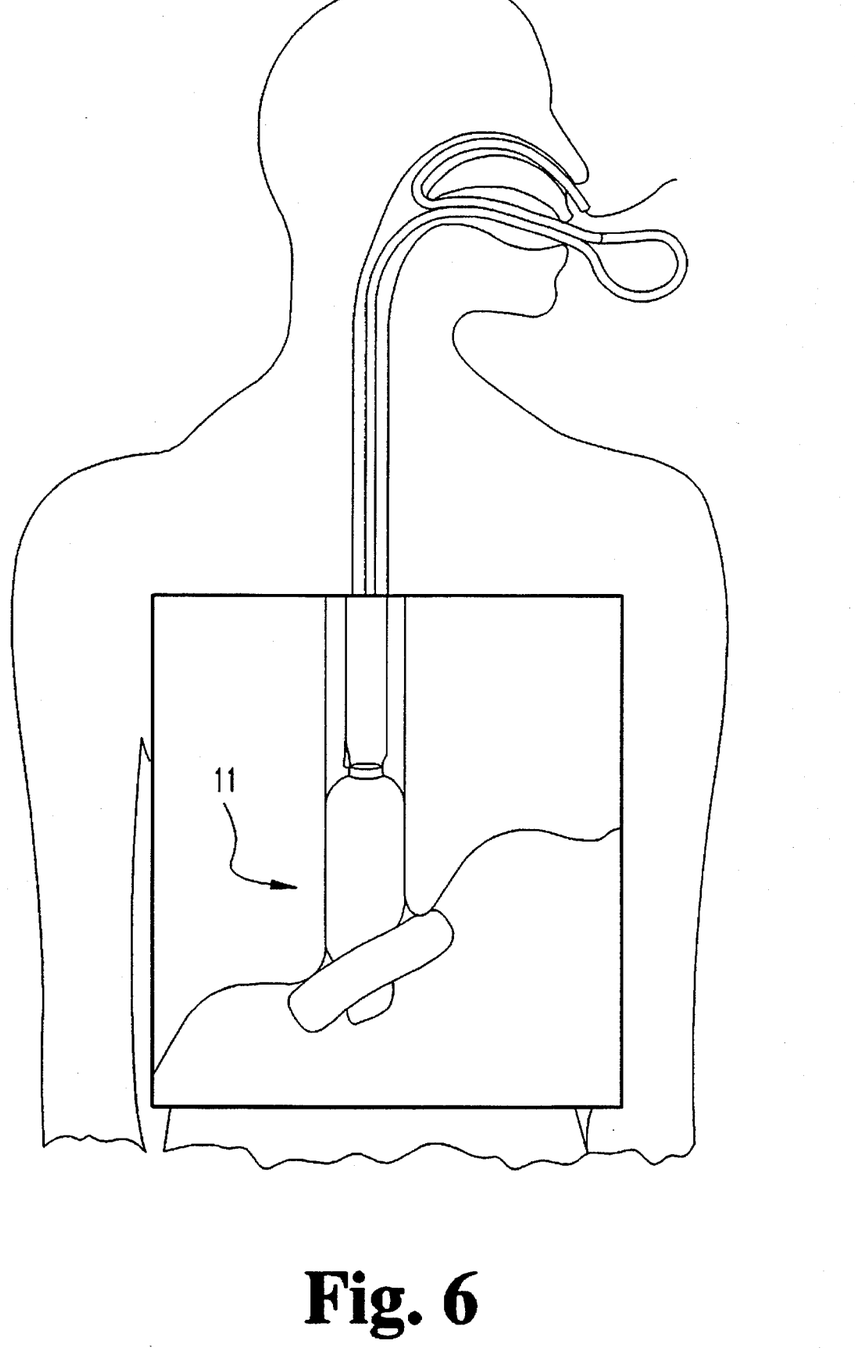
Figure 7:
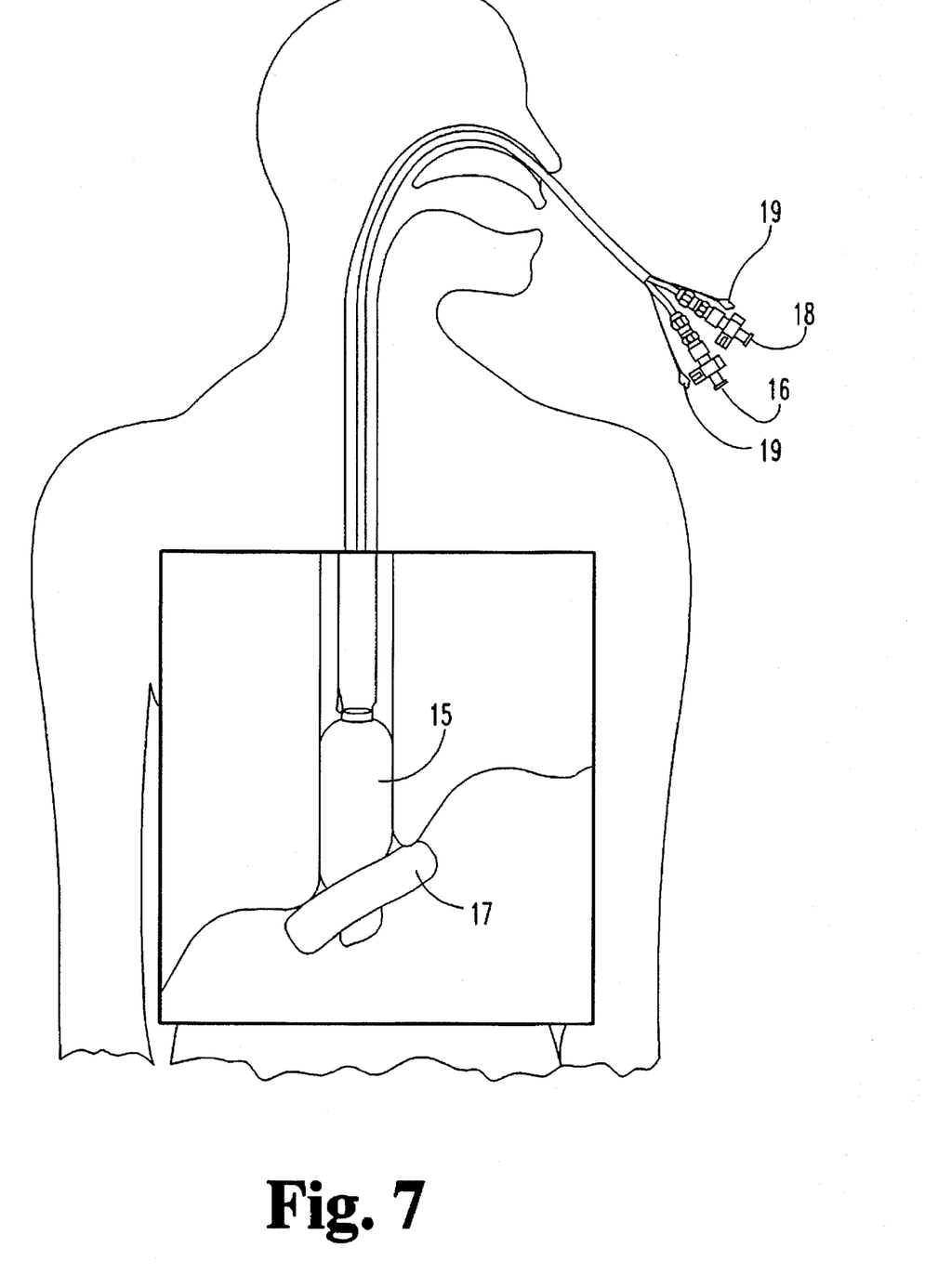

Additionally, prior to advancing the device down the esophagus, suitable hemostatic (such as microfibrillar collagen hemostat), coagulant (such as Thrombin, USP), or cytoprotective (such as sucralfate) substances can be applied to esophageal inflatable balloon 15 and/or gastric inflatable balloon 17. Such applications facilitate the later removal of the device by preventing adherence of the balloons to any bleeding sites. Referring to FIGS. 6 and 7, a preferred method for securing a bridle is shown. Once it has been confirmed that the device 11 is properly placed, a flexible guide tube having first and second open ends is provided. The first end of the guide tube is then placed through the nose and out the mouth of the patient, with the second end of the guide tube remaining external of the nose. Next, the bridle wires 19 and the inflation lumens 16 and 18, which are extending out of the mouth, are passed into said first end and out the second end of the guide tube. The guide tube is then withdrawn from the nose to leave bridle wires 19 and lumens 16 and 18 positioned through the patient's nose.

The established nasal bridle position is generally shown in FIG. 7. The gastric inflatable balloon 17 and the esophageal inflatable balloon 15 are inflated, and the wires 19 and the inflation lumens 16 and 18 are extending out of the nose. The appropriate connectors can then be placed on the inflation lumens 16 and 18 and the bridle wires 19 can be connected to a traction device as necessary. Having the lumens 16 and 18 and the bridle wires 19 positioned through the patient's nose increases patient comfort and reduces trauma to the nose and pharynx. Additionally, the wires 19 do not interfere with the use of an endoscope to periodically check the positioning of the device 11.

Figure 8:
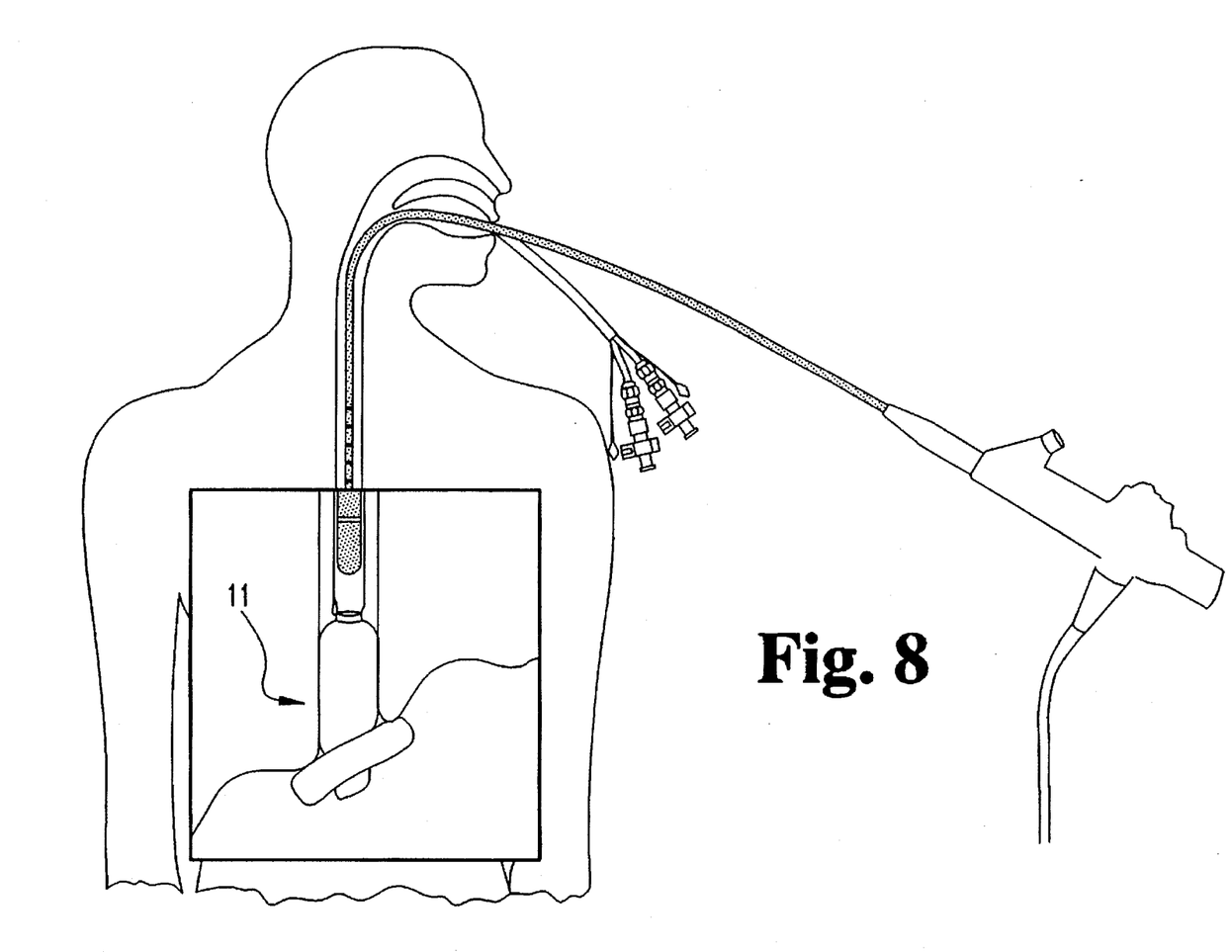

Referring to FIG. 8, with device 11 in place, the endoscope is brought into the esophagus and above device 11 to observe esophageal varices above the esophageal inflatable balloon 15. If the esophageal varices are collapsed, pressure in the esophageal inflatable balloon is slowly reduced until the varices distend and reappear. Pressure is then increased in the esophageal inflatable balloon while monitoring the inflation pressure. When the pressure inside the esophageal inflatable balloon is high enough to occlude blood flow in the portal veins traversing the diaphragmatic hiatus, the varices visible above the esophageal inflatable balloon collapse. The balloon pressure required to occlude these portal collateral veins is about identical to the pressure in the main portal vein to the liver. Upon occlusion, the balloons may be deflated to allow the esophageal varices to distend and this pressure is also measured. These endoscopically viewed points can be documented by endoscopic photography or video tape recording while a second blinded observer monitors the pressure within the balloons.

The anatomic configuration of esophagogastric collateral veins (varices) is like a step ladder with veins bulging into the esophagus and stomach connected by perforating veins to veins on or close to the serosal surface. Consequently pressure on the mucosal surface will not collapse the veins above the pressure point that are filled by perforating veins fed from serosal and exterior veins that bypass the point of pressure. The entire collateral circulation traversing the diaphragmatic hiatus must be occluded to collapse proximal veins and accurately measure portal pressure. This maneuver separates the portal collateral blood vessels from their high resistance exit site in the systemic circulation and breaks the resistance loop between the portal vein and collateral veins. This may be accomplished by a single esophageal balloon that tightly fits into the hiatus to compress all the traversing veins against the diaphragmatic hiatus or by using two balloons with a gastric balloon to compress the proximal stomach and adjacent veins against the diaphragm from below and a second esophageal balloon above the diaphragm to compress the esophagogastric junction against the gastric balloon. This serves to block collateral venous blood flow through a large diaphragmatic hiatus that would not be occluded by a single esophageal balloon.

Although a balloon is the preferred embodiment of this invention, it must be understood that similar functions could be served by any type of compression device including a disc or cage activated by gas pressure, a calibrated spring or any mechanical means. Although an optical or video endoscope utilizing direct operator observation is the preferred sensor for this invention, it must be understood that a similar function could be served by sonic, auditory or other sensors useful in detecting changes in tissue position, volume or blood flow.

Figure 9:
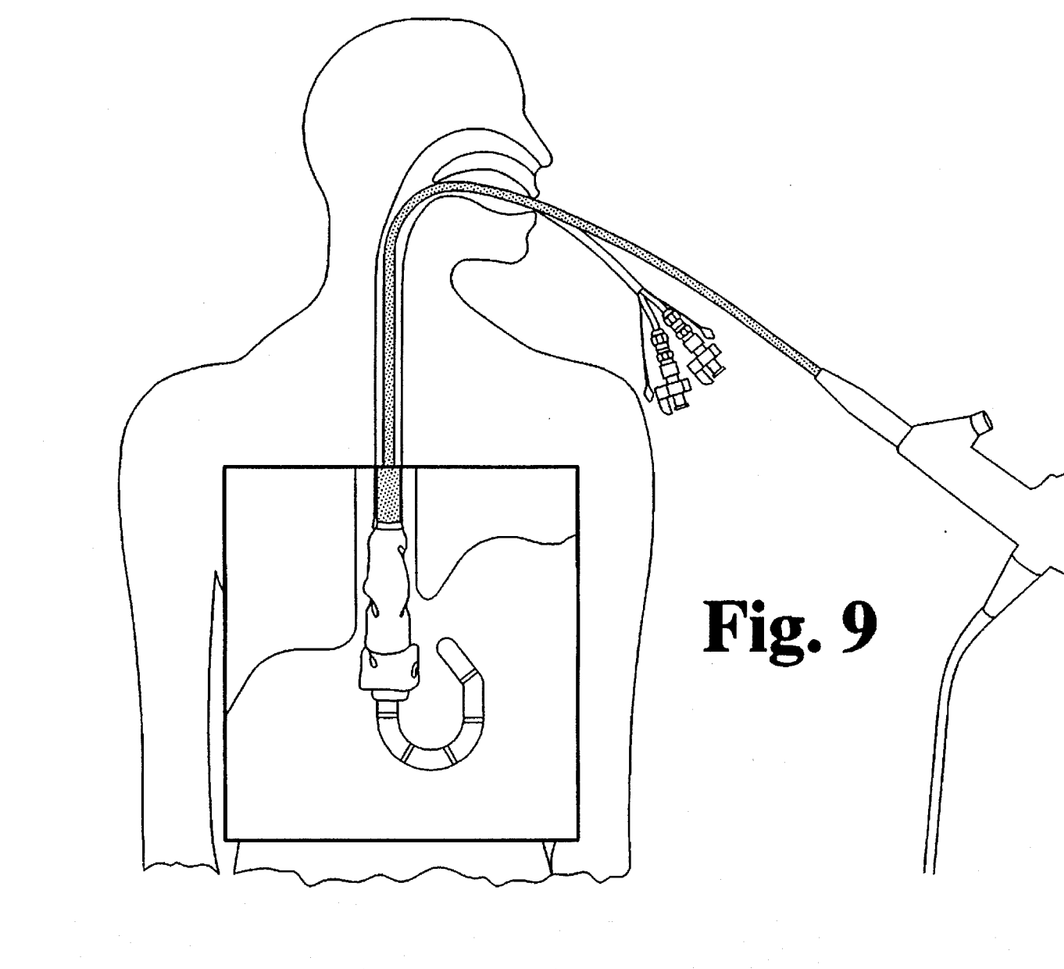
Figure 10:
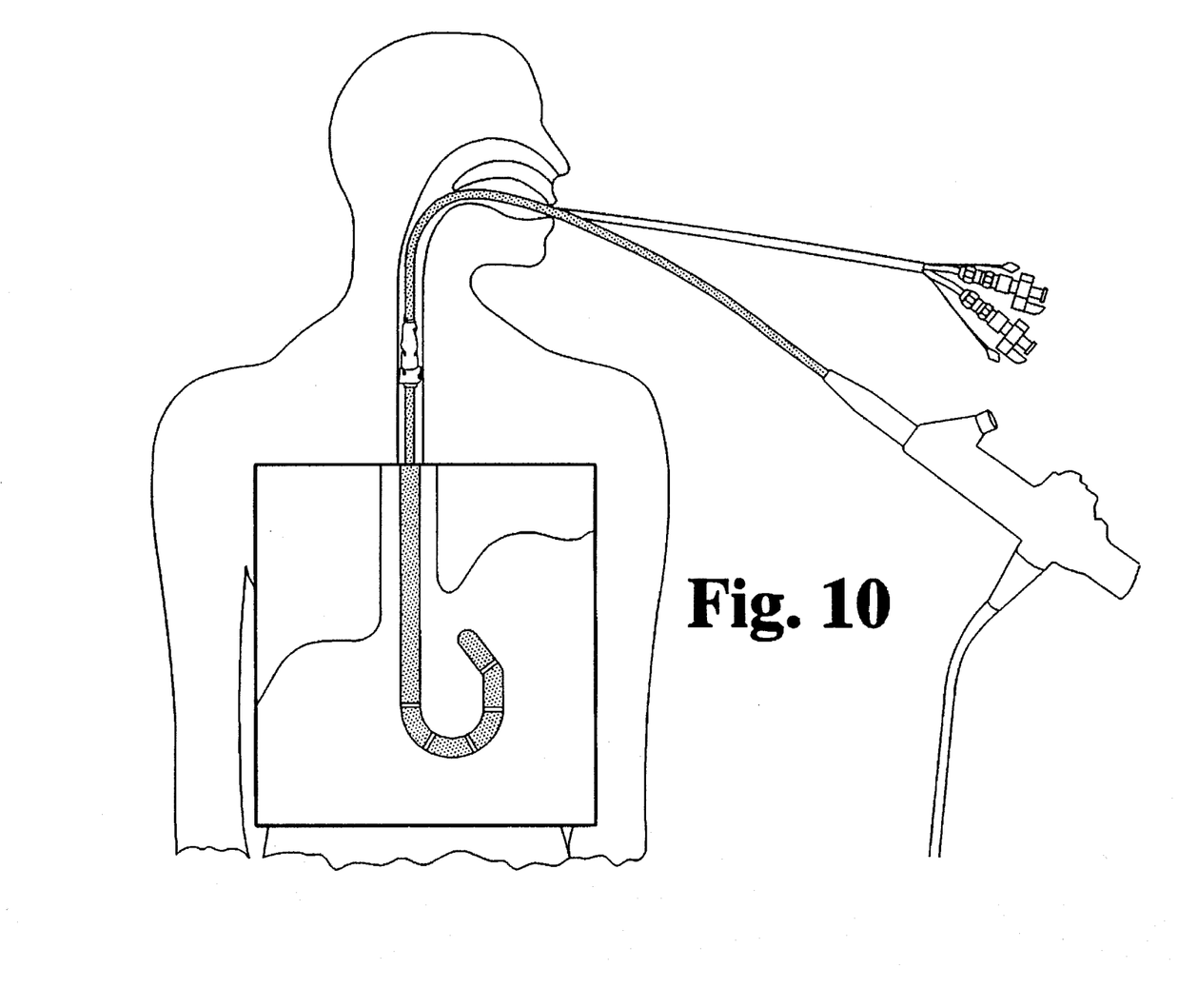

Referring to FIGS. 9 and 10, at the completion of the pressure measurement, the endoscope is placed through the device and into the stomach. The balloons are then deflated and the device 11 is pulled up the shaft of the endoscope. The endoscopy is then completed by examining the proximal stomach and distal esophagus to assure that there is no injury from the use of the device. Then, the endoscope, with the device 11, is removed from the patient.

While the invention has been illustrated and described in detail in the specification, these details are to be considered as illustrative and not restrictive. It should be understood that only a preferred embodiment is described and that all changes that come within the spirit of this invention are protected.

I claim:

1. A method for measuring portal blood pressure, comprising the steps of:

providing a device having an elongate member with proximal and distal ends, an esophageal inflatable balloon mounted over said member, and a first inflation lumen opening into said esophageal inflatable balloon;

passing said device down the esophagus and locating said esophageal inflatable balloon within the diaphragmatic hiatus;

positioning an endoscope above said device to observe esophageal varices;

inflating said esophageal inflatable balloon until the esophageal varices collapse; and measuring the pressure inside said esophageal inflatable balloon to indicate portal blood pressure.

2. The method of claim 1, further comprising deflating said esophageal inflatable balloon until the esophageal varices distend and measuring the pressure within the esophageal inflatable balloon.

3. The method of claim 1, wherein said providing step further includes a bridle attached to the proximal end of said member.

4. The method of claim 3, which further includes manipulating the bridle to position the proximal end of the member within the digestive tract and maintain the device in traction.

5. The method of claim 1, wherein in said providing step the elongate member is a tube.

6. The method of claim 1, wherein said providing step further includes a gastric inflatable balloon mounted over said member between said esophageal inflatable balloon and the distal end of said member, and a second inflation lumen opening into said gastric inflatable balloon.

7. The method of claim 6, further comprising before said inflating step, the steps of positioning said gastric inflatable balloon inside the stomach, inflating said gastric inflatable balloon, and seating said gastric inflatable balloon against the proximal stomach and the gastric cardia with traction.

8. The method of claim 7, further comprising after said seating step and before said inflating step, the steps of inflating said esophageal inflatable balloon to hold said device in place within the esophagus and removing the traction from said device.

9. The method of claim 7, further comprising the steps of gradually inflating said gastric inflatable balloon until the esophageal varices collapse and measuring the pressure inside said gastric inflatable balloon.

10. The method of claim 7, further comprising deflating said gastric inflatable balloon until the esophageal varices distend and measuring the pressure within the gastric inflatable balloon.

11. A method for measuring portal blood pressure, comprising the steps of:
providing a device having a tube with proximal and distal open ends, an esophageal inflatable balloon mounted over said tube, and a first inflation lumen opening into said esophageal inflatable balloon for directing pressurized fluid to inflate said esophageal inflatable balloon;
backloading said device on an endoscope by passing said endoscope through said open ends of said tube;
passing said endoscope down the esophagus;
advancing said device along said endoscope and down said esophagus to a location within the diaphragmatic hiatus;
inflating said esophageal inflatable balloon to fix said device into position in the diaphragmatic hiatus;
withdrawing said endoscope from said device and positioning said endoscope above said device to observe esophageal varices;
further inflating said esophageal inflatable balloon until blood flow in the portal veins traversing the diaphragmatic hiatus are occluded and observing the collapse of esophageal varices with said endoscope; and
measuring the pressure inside said esophageal inflatable balloon in order to obtain an indication of the portal blood pressure.

12. The method of claim 11, further comprising deflating said esophageal inflatable balloon until the esophageal varices distend and measuring the pressure within said esophageal inflatable balloon.

13. The method of claim 11, wherein said providing step further includes a bridle attached to said tube, said bridle adapted to extend up the esophagus to a traction means.

14. The method of claim 13, which further includes manipulating the bridle to position the proximal end of the member within the digestive tract and maintain the device in traction.

15. The method of claim 11, wherein said providing step further includes a gastric inflatable balloon mounted over said tube between said esophageal inflatable balloon and the distal end of said tube, and a second inflation lumen opening into said gastric inflatable balloon for directing pressurized fluid to inflate said gastric balloon.

16. The method of claim 15, further comprising before said inflating step, the steps of positioning said gastric balloon inside the stomach, inflating said gastric balloon, and pulling said gastric balloon against the proximal stomach and the diaphragmatic hiatus with a traction means to seat said gastric balloon against the gastric cardia.

17. The method of claim 16, further comprising after said inflating step, the step of releasing said traction means, whereby said device moves with respiration and is fixed across the diaphragmatic hiatus.

18. The method of claim 17, further comprising the steps of inflating said gastric balloon until blood flow in the portal veins traversing the diaphragmatic hiatus are occluded and measuring the pressure inside said gastric balloon.

19. The method of claim 18, further comprising deflating said gastric balloon until the esophageal varices distend and measuring the pressure within the gastric balloon.

20. A method for measuring portal venous blood pressured, comprising the steps of:
providing a device having a tube with proximal and distal open ends, an esophageal inflatable balloon mounted over said tube, a first inflation lumen opening into said esophageal inflatable balloon for directing pressurized fluid to inflate said esophageal inflatable balloon, a gastric inflatable balloon mounted over said tube between said esophageal inflatable balloon and said distal open end, and a second inflation lumen opening into said gastric inflatable balloon for directing pressurized fluid to inflate said gastric balloon;
backloading said device on an endoscope by passing said endoscope through said open ends of said tube;
passing said endoscope down the esophagus;
advancing said device along said endoscope and down said esophagus to a location within the diaphragmatic hiatus;
positioning said gastric balloon inside the stomach and inflating said gastric balloon;
pulling said gastric balloon against the proximal stomach and the diaphragmatic hiatus with a traction means to seat said gastric balloon against the gastric cardia;
inflating the esophageal inflatable balloon to fix said device across the diaphragmatic hiatus;
releasing said traction means;
locating said endoscope to a position above the esophageal inflatable balloon, whereby esophageal varices may be observed;
gradually inflating said balloons until blood flow in the portal veins traversing the diaphragmatic hiatus occludes, whereby the esophageal varices collapse; and
measuring the pressure inside said esophageal inflatable balloon and said gastric inflatable balloon to obtain an indication of the portal blood pressure.

21. The method of claim 20, further comprising deflating said esophageal inflatable balloon and said gastric inflatable balloon until the esophageal varices distend and measuring the pressure within said balloons.

22. The method of claim 20, wherein said providing step further includes a bridle attached to said tube, said bridle adapted to extend up the esophagus to a traction means.

23. The method of claim 22, which further includes manipulating the bridle to position the proximal end of the member within the digestive tract and maintain the device in traction.

* * * * *